United States Patent
Hayakawa et al.

(10) Patent No.: US 7,652,276 B2
(45) Date of Patent: Jan. 26, 2010

(54) DEFECT INSPECTION METHOD, DEFECT INSPECTION APPARATUS HAVING A MOUNTING TABLE WITH A SUBSTRATE THEREON AND AN IMAGE PICKUP DEVICE ARE RELATIVELY MOVED FOR CAPTURING THE IMAGE OF THE SUBSTRATE, AND COMPUTER READABLE STORAGE MEDIUM STORING A PROGRAM FOR PERFORMING THE METHOD

(75) Inventors: Makoto Hayakawa, Koshi (JP); Hiroshi Tomita, Koshi (JP)

(73) Assignee: Tokyo Electron Limited, Tokyo (JP)

( * ) Notice: Subject to any disclaimer, the term of this patent is extended or adjusted under 35 U.S.C. 154(b) by 553 days.

(21) Appl. No.: 11/698,049

(22) Filed: Jan. 26, 2007

(65) Prior Publication Data
US 2007/0188832 A1 Aug. 16, 2007

(30) Foreign Application Priority Data
Feb. 8, 2006 (JP) ............... 2006-031126
Jan. 10, 2007 (JP) ............... 2007-002440

(51) Int. Cl.
*G01N 21/86* (2006.01)
(52) U.S. Cl. .................. 250/559.4; 250/208.1
(58) Field of Classification Search .......... 250/559.4, 250/221, 208.1, 559.45, 559.2, 234, 235; 356/237.2–237.5; 369/44.26–44.33; 347/224, 347/225; 118/676–690
See application file for complete search history.

(56) References Cited

U.S. PATENT DOCUMENTS 6,004,047 A 12/1999 Akimoto et al.
7,436,420 B2 * 10/2008 Honda et al. ............ 347/224

FOREIGN PATENT DOCUMENTS

| JP | 10-247621 | 9/1998 |
| JP | 11-167210 | 6/1999 |
| JP | 2001-168010 | 6/2001 |
| JP | 2002-267616 | 9/2002 |
| JP | 2003-289030 | 10/2003 |
| JP | 2006-049630 | 2/2006 |

* cited by examiner

*Primary Examiner*—Que T Le
(74) *Attorney, Agent, or Firm*—Smith, Gambrell & Russell, LLP

(57) ABSTRACT

In the present invention, an image pickup device moving by drive of a drive unit picks up an image of a substrate on a mounting table. The drive unit is controlled by a driving signal from a first controller. The driving signal outputted to the first controller is outputted also to a second controller, so that the second controller controls the image pickup device based on the driving signal. The movement of the image pickup device itself is synchronized with the image pickup by the image pickup device. According to the present invention, at the time when the mounting table mounting the substrate thereon and the image pickup device are relatively moved to capture the image of the substrate, a precise image without image distortion can be captured for accurate inspection.

15 Claims, 13 Drawing Sheets

DEFECT INSPECTION METHOD, DEFECT INSPECTION APPARATUS HAVING A MOUNTING TABLE WITH A SUBSTRATE THEREON AND AN IMAGE PICKUP DEVICE ARE RELATIVELY MOVED FOR CAPTURING THE IMAGE OF THE SUBSTRATE, AND COMPUTER READABLE STORAGE MEDIUM STORING A PROGRAM FOR PERFORMING THE METHOD

BACKGROUND OF THE INVENTION

1. Field of the Invention

The present invention relates to a substrate defect inspection method, a defect inspection apparatus, and a computer readable storage medium.

2. Description of the Related Art

In a photolithography process in a manufacturing process of a semiconductor device, for example, a resist coating treatment for forming a resist film on a front surface of a substrate such as a wafer, exposure processing for exposure by irradiating a pattern on the front surface of the substrate, a developing treatment for developing the substrate after the exposure and so on are performed. The substrate for which a series of predetermined photolithography process is subjected to a so-called macro defect inspection by an inspection apparatus, such as whether or not a predetermined resist film is formed on the front surface of the substrate, or whether or not appropriate exposure processing is performed, and whether or not there is a scratch, or adherence of foreign substance.

The macro defect inspection is performed such that an image pickup device, such as a CCD line sensor is moved relative to a mounting table mounting a substrate thereon to capture an image of the substrate and perform image processing on the image so as to determined presence or absence of a defect (Japanese Patent Application Laid-open No. 2002-267616).

SUMMARY OF THE INVENTION

To perform the above-described macro defect inspection, an image at a high level necessary for the defect inspection is required. It is difficult, however, to capture such an image at a high level only by relative movement of the image pickup device and the mounting table to capture an image of the substrate as in the prior art. When the relative moving speed is greater than the image capture cycle of the image pickup device, the captured image will shrink in the moving direction and, in contrast, when the moving speed is less than the cycle, the image will expand in the moving direction.

The present invention has been developed in consideration of the above viewpoints, and its object is to capture a precise image without image distortion at the time when the mounting table mounting the substrate thereon and the image pickup device are relatively moved to capture an image of the substrate.

To achieve the above object, the present invention is a method of picking up an image of a substrate on a mounting table by an image pickup device while relatively moving the image pickup device and the substrate in a predetermined direction to inspect the substrate for a defect, wherein drive of the image pickup device or the mounting table to realize the relative movement is synchronized with the image pickup by the image pickup device when the image pickup device picks up the image of the substrate.

The relative movement between the image pickup device and the substrate on the mounting table is synchronized with the image pickup by the image pickup device as described above, whereby a precise image without image distortion can be obtained. Relatively moving the image pickup device and the substrate on the mounting table in a predetermined direction refers to moving at least one of the image pickup device and the substrate on the mounting table (or the mounting table having the substrate mounted thereon) in a predetermined direction. Therefore, the relative movement also includes movement of only the image pickup device, conversely, movement of only the substrate on the mounting table (or the mounting table having the substrate mounted thereon), or movement of both of them.

For synchronization, image capture by the image pickup device may be controlled based on a driving signal outputted from a controller to a drive unit for driving the image pickup device or the mounting table.

Further, image capture by the image pickup device may be controlled based on a feedback signal, for example, an encoder signal outputted to a controller from a drive unit for driving the image pickup device or the mounting table. Generally, when the image pickup device or the mounting table is moved by the drive unit, for example, a pulse motor, the encoder signal indicating that it is moved is outputted every second from the drive unit side. Accordingly, the synchronization may be performed based on the feedback signal such as the encoder signal.

Other than the control of the image capture by the image pickup device based on the driving signal used for the drive unit as described above, drive of the image pickup device or the mounting table, for example, the driving speed may be controlled based on a control signal for controlling a capture timing or capture cycle of image by the image pickup device. In this case, the image capture timing is preferably changed depending on a luminance on the substrate.

In the defect inspection method, the image pickup device may pick up the image of the substrate on the mounting table with the image pickup device fixed and the mounting table being moved with respect to the image pickup device.

The defect inspection method as described above may be performed by a computer program installed in an appropriate controller, or recorded on a readable storage medium, such as a hard disk, compact disk, flexible disk, magneto-optical disk, or the like.

According to another aspect, the present invention is an apparatus for picking up an image of a substrate on a mounting table by an image pickup device while relatively moving the image pickup device and the substrate on the mounting table in a predetermined direction by a drive unit to inspect the substrate for a defect, including a first controller for controlling the drive unit; and a second controller for controlling the image pickup by the image pickup device. Further, a driving signal outputted from the first controller or outputted to the first controller in order to drive the drive unit is outputted also to the second controller, and the second controller is configured to control the image pickup by the image pickup device based on the driving signal.

According to still another aspect, the present invention is an apparatus for picking up an image of a substrate on a mounting table by an image pickup device while relatively moving the image pickup device and the substrate on the mounting table in a predetermined direction by a drive unit to inspect the substrate for a defect, including a first controller for controlling the drive unit; and a second controller for controlling the image pickup by the image pickup device. Further, a feedback signal outputted from the drive unit to the first controller is outputted also to the second controller from the first controller directly or via another controller, and the second controller is configured to control the image pickup by the image pickup device based on the feedback signal.

According to yet another aspect, the present invention is an apparatus for picking up an image of a substrate on a mounting table by an image pickup device while relatively moving the image pickup device and the substrate on the mounting table in a predetermined direction by a drive unit to inspect the substrate for a defect, including a first controller for controlling the drive unit; and a second controller for controlling the image pickup by the image pickup device. Further, the second controller includes a reference clock for controlling a timing of image capture by the image pickup device, a driving signal is outputted to the first controller directly or via another controller based on the reference clock, and the first controller is configured to control the drive unit based on the driving signal.

In this case, the apparatus may further include a control unit for changing a cycle of the reference clock based on luminance information on the substrate being an image pickup object. The reference clock may be provided in the image pickup device or the other controller. Further, the above-described defect inspection apparatus may be configured such that the image pickup device picks up the image of the substrate on the mounting table with the image pickup device fixed and the mounting table being moved with respect to the image pickup device by the drive unit.

According to the present invention, at the time when picking up an image of a substrate on a mounting table by an image pickup device while relatively moving the image pickup device and the substrate on the mounting table in a predetermined direction to inspect the substrate for a defect, drive of the image pickup device or the mounting table to realize the relative movement is synchronized with the image pickup by the image pickup device, thereby allowing a precise image to be captured for inspection.

DETAILED DESCRIPTION OF THE INVENTION

Figure 1:
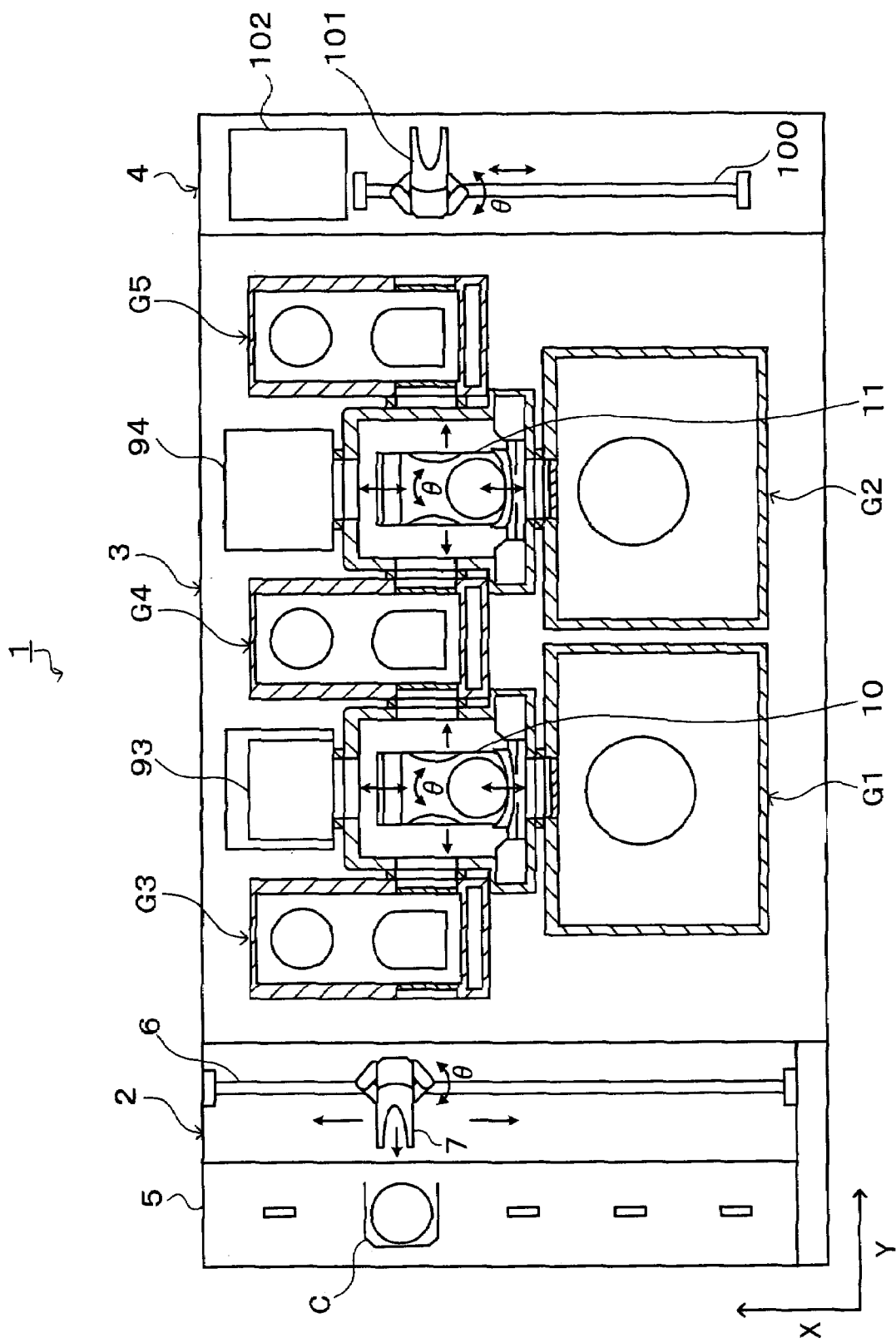
FIG. 1 is an explanatory view of the plane of a coating and developing treatment system including a defect inspection apparatus according to an embodiment.
Figure 2:
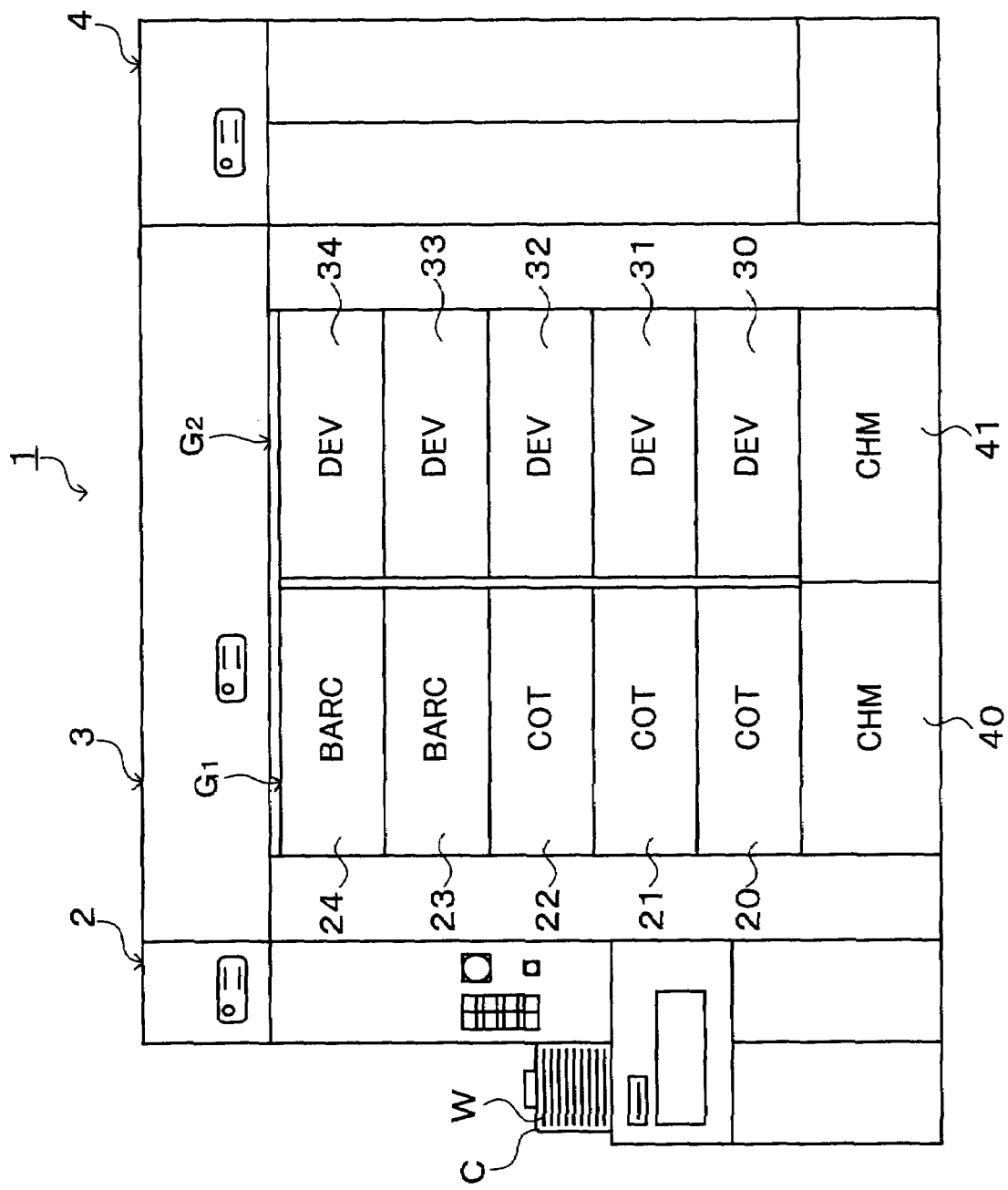
FIG. 2 is an explanatory view of the front of the coating and developing treatment system in FIG. 1.
Figure 3:
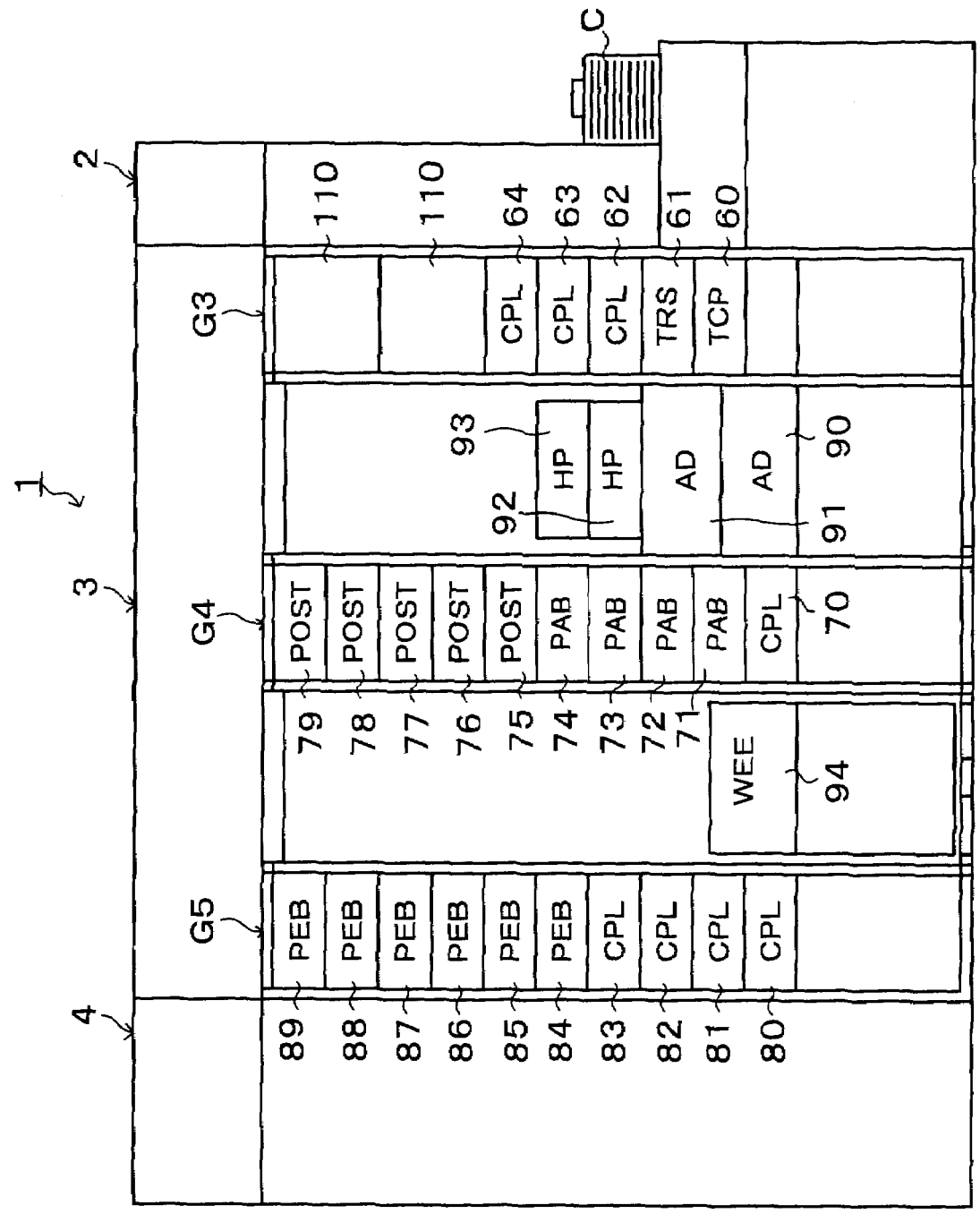
FIG. 3 is an explanatory view of the rear of the coating and developing treatment system in FIG. 1.

Hereinafter, preferred embodiments of the present invention will be described. FIG. 1 is a plan view showing the outline of a configuration of a coating and developing treatment system 1 in which a defect inspection apparatus according to the present embodiment is incorporated, FIG. 2 is a front view of the coating and developing treatment system 1, and FIG. 3 is a rear view of the coating and developing treatment system 1.

The coating and developing treatment system 1 has, as shown in FIG. 1, a configuration in which, for example, a cassette station 2 for transferring, for example, 25 wafers W per cassette as a unit from/to the outside into/from the coating and developing treatment system 1 and transferring the wafers W into/out of a cassette C; a processing station 3 including a plurality of various kinds of processing and treatment units, which are multi-tiered, for performing predetermined processing or treatment in a manner of single wafer processing in a photolithography process; and an interface section 4 for passing the wafer W to/from an aligner (not shown) provided adjacent to the processing station 3, are integrally connected.

In the cassette station 2, a cassette mounting table 5 is provided and configured such that a plurality of cassettes C can be mounted on the cassette mounting table 5 in a line in an X-direction (a top-to-bottom direction in FIG. 1). In the cassette station 2, a wafer transfer body 7 is provided which is movable in the X-direction on a transfer path 6. The wafer transfer body 7 is also movable in a wafer-arrangement direction of the wafers W housed in the cassette C (a Z-direction; the vertical direction), and thus can selectively access the wafers W in each of the cassettes C arranged in the X-direction.

The wafer transfer body 7 is rotatable in a θ-direction around the Z-axis, and can access a temperature regulating unit 60 and a transition unit 61 which are included in a later-described third processing unit group G3 on the processing station 3 side.

The processing station 3 adjacent to the cassette station 2 includes, for example, five processing unit groups G1 to G5 in each of which a plurality of processing and treatment units are multi-tiered. On the side of the negative direction in the X-direction (the downward direction in FIG. 1) in the processing station 3, the first processing unit group G1 and the second processing unit group G2 are placed in order from the cassette station 2 side. On the side of the positive direction in the X-direction (the upward direction in FIG. 1), in the processing station 3, the third processing unit group G3, the fourth processing unit group G4, and the fifth processing unit group G5 are placed in order from the cassette station 2 side. Between the third processing unit group G3 and the fourth processing unit group G4, a first transfer unit 10 is provided. The first transfer unit 10 can selectively access the processing and treatment units in the first processing unit group G1, the third processing unit group G3, and the fourth processing unit group G4 and transfer the wafer W to them. Between the fourth processing unit group G4 and the fifth processing unit group G5, a second transfer unit 11 is provided. The second transfer unit 11 can selectively access the processing and treatment units in the second processing unit group G2, the fourth processing unit group G4, and the fifth processing unit group G5 and transfer the wafer W to them.

In the first processing unit group G1, as shown in FIG. 2, solution treatment units each for supplying a predetermined liquid to the wafer W to perform treatment, for example, resist coating units 20, 21, and 22 each for applying a resist solution to the wafer W, and bottom coating units 23 and 24 each for forming an anti-reflection film that prevents reflection of light at the time of exposure processing, are five-tiered in order from the bottom. In the second processing unit group G2, solution treatment units, for example, developing treatment units 30 to 34 each for supplying a developing solution to the wafer W to develop it are five-tiered in order from the bottom. Further, chemical chambers 40 and 41 each for supplying various kinds of treatment solutions to the solution treatment units in the processing unit groups G1 and G2 are provided on the lowermost tiers of the first processing unit group G1 and the second processing unit group G2, respectively.

As shown in FIG. 3, in the third processing unit group G3, for example, the temperature regulating unit 60, the transition unit 61 for passing the wafer W, high-precision temperature regulating units 62 to 64 each for temperature-regulating the wafer W under temperature control with a high precision, and defect inspection apparatuses 110 according to the present embodiment are seven-tiered in order from the bottom. Note that the configuration of the defect inspection apparatus 110 will be described later.

In the fourth processing unit group G4, for example, a high-precision temperature regulating unit 70, pre-baking units 71 to 74 each for heating the wafer W coated with the resist solution, post-baking units 75 to 79 each for heat-processing the wafer W after developing treatment, are ten-tiered in order from the bottom.

In the fifth processing unit group G5, a plurality of thermal processing units each for performing thermal processing for the wafer W, for example, high-precision temperature regulating units 80 to 83, and a plurality of post-exposure baking units 84 to 89 each for heat-processing the wafer W after exposure, are ten-tiered in order from the bottom.

As shown in FIG. 1, a plurality of processing and treatment units are arranged on the positive direction side in the X-direction of the first transfer unit 10, for example, adhesion units 90 and 91 each for performing hydrophobic treatment on the wafer W and heating units 92 and 93 each for heating the wafer W being four-tiered in order from the bottom as shown in FIG. 3. As shown in FIG. 1, on the positive direction side in the X-direction of the second transfer unit 11, for example, an edge exposure unit 94 is disposed which selectively exposes only the edge portion of the wafer W to light.

In the interface section 4, for example, a wafer transfer body 101 moving on a transfer path 100 extending in the X-direction and a buffer cassette 102 are provided as shown in FIG. 1. The wafer transfer body 101 is movable in the Z-direction and also rotatable in the θ-direction and thus can access the not-shown aligner adjacent to the interface section 4, the buffer cassette 102, and the fifth processing unit group G5 and transfer the wafer W to them.

Figure 4:
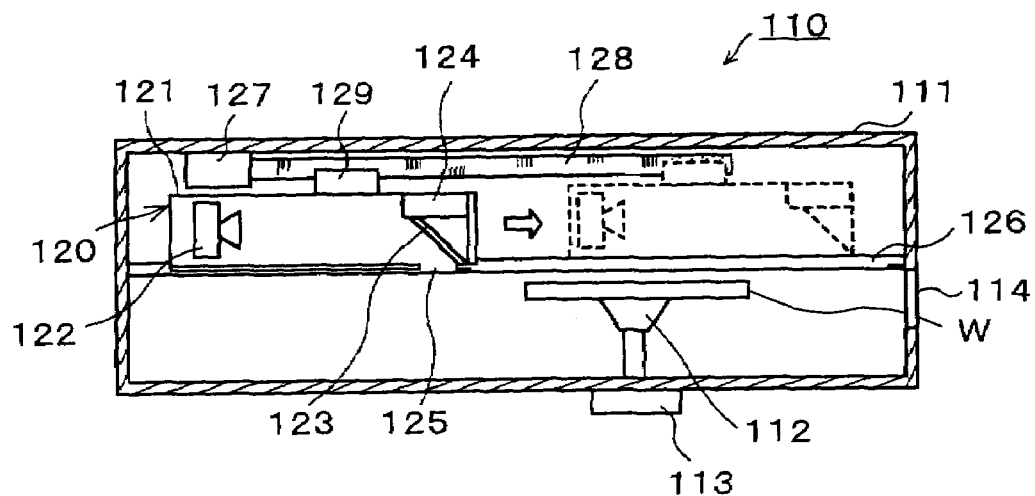
FIG. 4 is an explanatory view of a side section of a defect inspection apparatus according to the embodiment.
Figure 5:
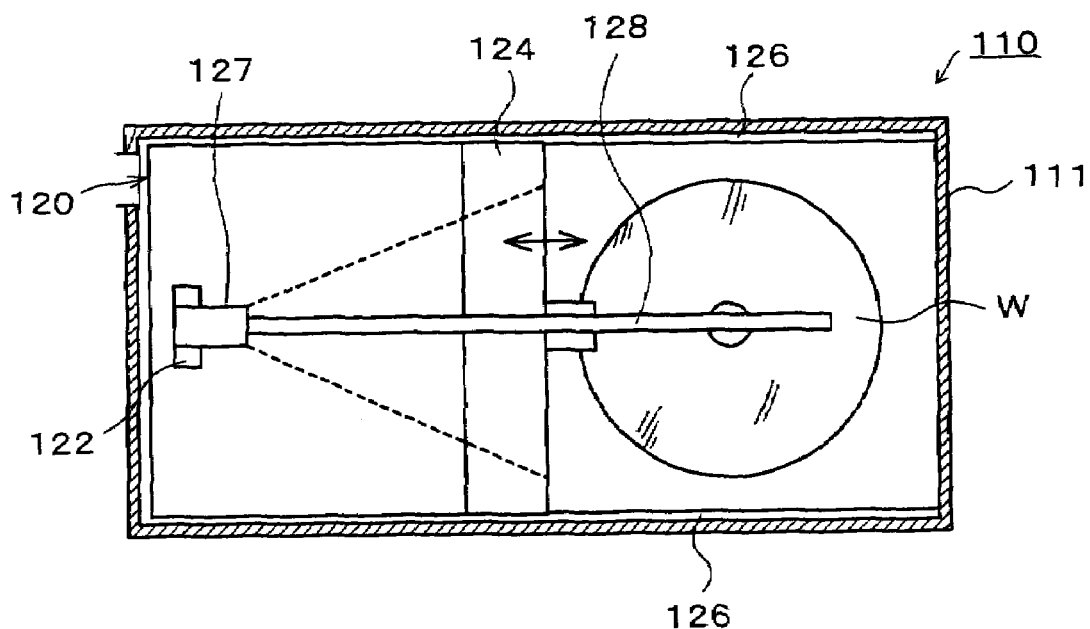
FIG. 5 is an explanatory view of a plane section of the defect inspection apparatus according to the embodiment.

Next, the defect inspection apparatus 110 incorporated in the coating and developing treatment system 1 according to the above configuration will be described. FIG. 4 shows a side section of the defect inspection apparatus 110, and FIG. 5 shows a plane section of the same.

The defect inspection apparatus 110 has an image pickup unit 120 in an upper space in a casing 111 covering its outside. The image pickup unit 120 has an image pickup device 122 at one end portion within a cover 121 having an outer shape in an almost rectangular parallelepiped. This embodiment employs a wide-angle CCD camera. On the other end side within the cover 121, a half mirror 123 is provided. Behind the half mirror 123, an illumination device 124 is provided. An opening 125 is formed in a lower surface of the other end portion of the cover 121, so that illumination from the illumination device 124 passes through the half mirror 123 and is applied from the opening 125 to below the image pickup unit 120. Accordingly, reflected light off an object lying within the irradiation region is reflected by the half mirror 123 and captured into the image pickup device 122. In other words, the image pickup device 122 can pick up the image of the object lying within the irradiation region.

The image pickup unit 120 is linearly movable in the casing 111 of the defect inspection apparatus 110 as shown with an arrow in the drawing. In this embodiment, the image pickup unit 120 moves along guide rails 126 provided on both sides in the casing 111. Drive of the image pickup unit 120 is performed by drive of a drive unit 127, for example, a pulse motor or the like. More specifically, a slider 129 secured to the cover 121 of the image pickup unit 120 meshes with a drive shaft 128 rotating by the drive of the drive unit 127, so that the image pickup unit 120 having the slider 129 linearly moves in the casing 111 of the defect inspection apparatus 110 by rotation of the drive shaft 128 by the drive unit 127 like the ball screw configuration. Note that the guide rails 126 may be provided on both sides of the drive shaft 128 or may be integrated with the drive shaft 128.

On the side of an end portion in the lower space in the casing 111, a mounting table 112 is provided which mounts the wafer W thereon. The mounting table 112 is freely rotated and stopped by a rotation drive unit 113 such as a motor, and has an alignment function. Note that on an end portion in the casing 111, a transfer-in/out port 114 is provided for transferring-in and transferring-out the wafer W to/from the mounting table 112 in the image pickup unit 120.

With the defect inspection apparatus 110 having the above configuration, the image pickup unit 120 can scan the top surface of the wafer W on the mounting table 112 while moving along the guide rails 126 in the upper space within the casing 111 to pick up an image of the entire surface of the wafer W by the image pickup device 122.

Figure 6:
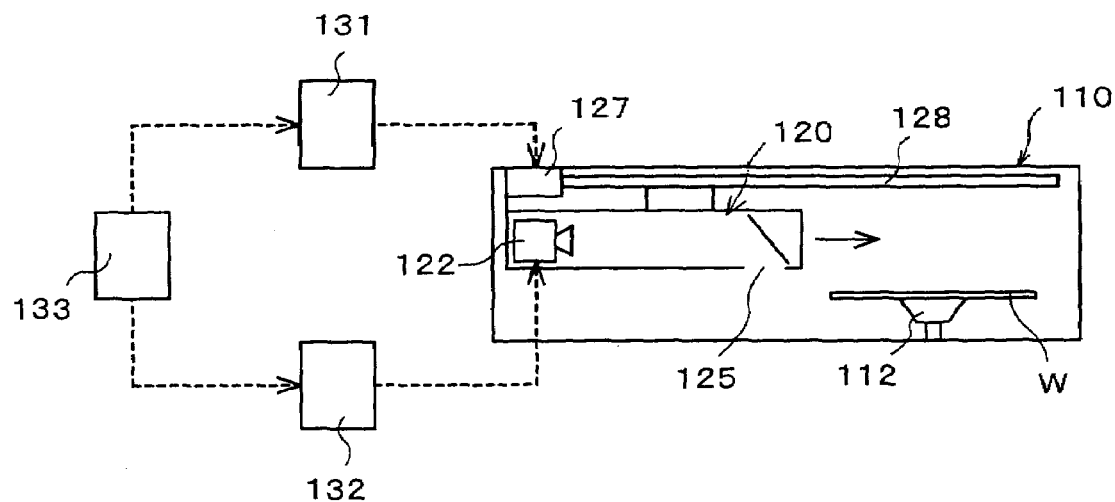
FIG. 6 is an explanatory view showing the outline of a configuration of a control system of the defect inspection apparatus according to the embodiment.

Describing a control system of the defect inspection apparatus 110 according to this embodiment, drive of the drive unit 127, such as, ON, OFF, speed and the like is controlled by a first controller 131 as shown in FIG. 6. More specifically, drive, stop, even drive speed, and so on of the drive unit 127 are controlled by a driving signal outputted from the first controller 131 to the drive unit 127. An encoder signal at that time is then outputted from the drive unit 127 driven by the driving signal to the first controller 131.

The image pickup device 122 is controlled by a second controller 132. In this embodiment, image pickup by the image pickup device 122, an image pickup timing, an image capture time, and so on are controlled by an external synchronization signal outputted from the second controller 132 to the image pickup device 122. The picked-up image is then outputted to the second controller 132 and subjected to necessary image-processing in the second controller 132 or a third controller 133.

The first controller 131 and the second controller 132 are controlled by the higher third controller 133 which controls the whole coating and developing treatment system 1. In other words, based on a driving signal outputted from the third controller 133 to the first controller 131, the first controller 131 outputs a predetermined driving signal to the drive unit 127. On the other hand, the third controller 133 outputs the driving signal also to the second controller 132 at the same timing with the driving signal outputted to the first controller 131, so that the second controller 132 outputs the external synchronization signal to the image pickup device 122 based on the driving signal. In this case, the relation between the driving signal and the external synchronization signal may be such that a synchronization signal is for picking up an image of one shot (one line) for one pulse of driving signal or a synchronization signal is for picking up an image of one shot (one line) for a plurality of pulses.

The control as described above is conducted following a computer program, for example, recorded in the third controller 133, or recorded in various kinds of storage media readable in the third controller 133.

The defect inspection apparatus 110 according to this embodiment has the configuration as described above, in which when the wafer W being an inspection object is mounted on the mounting table 112 in the defect inspection apparatus 110, a predetermined alignment is performed, and the image pickup unit 120 is then moved so that image pickup of the wafer W is performed by the image pickup device 122 in the image pickup unit 120.

In this case, to drive the image pickup unit 120, the driving signal is outputted from the third controller 133 to the first controller 131, based on which the first controller 131 outputs a predetermined driving signal to the drive unit 127. In this event, the third controller 133 outputs the driving signal also to the second controller 132 at the same time, based on which the external synchronization signal is outputted from the second controller 132 to the image pickup device 122, based on which the image pickup device 122 picks up an image of the wafer W on the mounting table 112, whereby the image pickup by the image pickup device 122 is synchronized with the movement of the image pickup unit 120, that is, the movement of the image pickup device 122. Accordingly, even if the image pickup device 122 picks up an image of the wafer W on the mounting table 112 while the image pickup unit 120, that is, the image pickup device 122 is moving as described above, a precise image can be obtained to realize a defect inspection with high precision.

Figure 7:
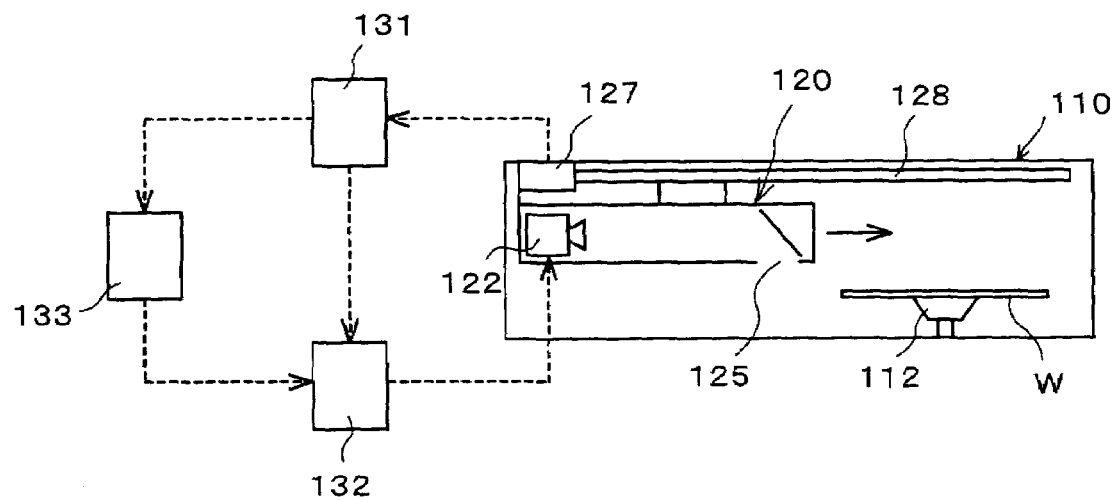
FIG. 7 is an explanatory view showing the outline of a configuration of a control system of a defect inspection apparatus according to another embodiment.

Concurrently with the output of the driving signal to the first controller 131, the third controller 133 outputs the driving signal to the second controller 132, based on which the second controller 132 outputs the external synchronization signal to the image pickup device 122 in the above embodiment. In place of the configuration, for example, the feedback signal, for example, the encoder signal outputted from the drive unit 127 to the first controller 131 may be outputted directly to the second controller 132, or outputted to the second controller 13 via the third controller 133 as shown in FIG. 7, so that the second controller 132 outputs the external synchronization signal to the image pickup device 122 based on the feedback signal.

Figure 8:
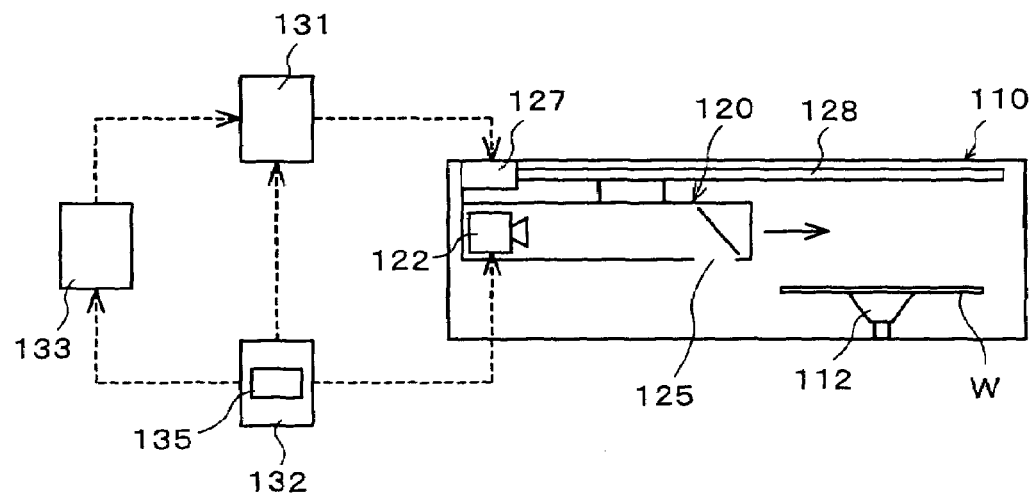
FIG. 8 is an explanatory view showing the outline of a configuration of a control system of a defect inspection apparatus according to another embodiment.

Although the external synchronization signal is outputted to the image pickup device 122 based on the driving signal or the feedback signal on the side of the drive unit 127 moving the image pickup device 122 itself in the above configuration, drive on the drive unit 127 side may be controlled based on the signal on the image pickup device 122 side. For example, if the second controller 132 has a reference clock 135 being a reference for outputting the external synchronization signal to the image pickup device 122 as shown in FIG. 8, image pickup by the image pickup device 122 can be synchronized with movement of the image pickup device 122 itself by directly outputting the driving signal based on the reference clock 135 to the first controller 131 or outputting the driving signal to the first controller 131 via the third controller 133. Note that the reference clock 135 may be provided in the image pickup device 122 or the third controller 133.

Incidentally, the luminance (brightness and darkness) on the wafer W may be different due to the difference in reflectivity of the front surface of the wafer W depending on the state of the wafer W to be inspected, and therefore when an image is picked up using the same image capture time for every case, the captured image is so-called overexposed or underexposed, failing to obtain an image with high precision. In this case, for example, the illuminance by the illumination device 124 may be changed depending on the brightness on the wafer W, but there is a case using the illumination device which cannot be changed as describe above, or a case in which the illumination device varies in conditions when the illuminance is changed to fail to, for example, collate, compare and so on with the reference wafer. In this case, the length of the image capture cycle will be changed. In such a case, according to the change, drive, such as the moving speed, of the image pickup device 122 (the image pickup unit 120) itself by the drive unit 127 needs to be changed as a matter of course.

Figure 9:
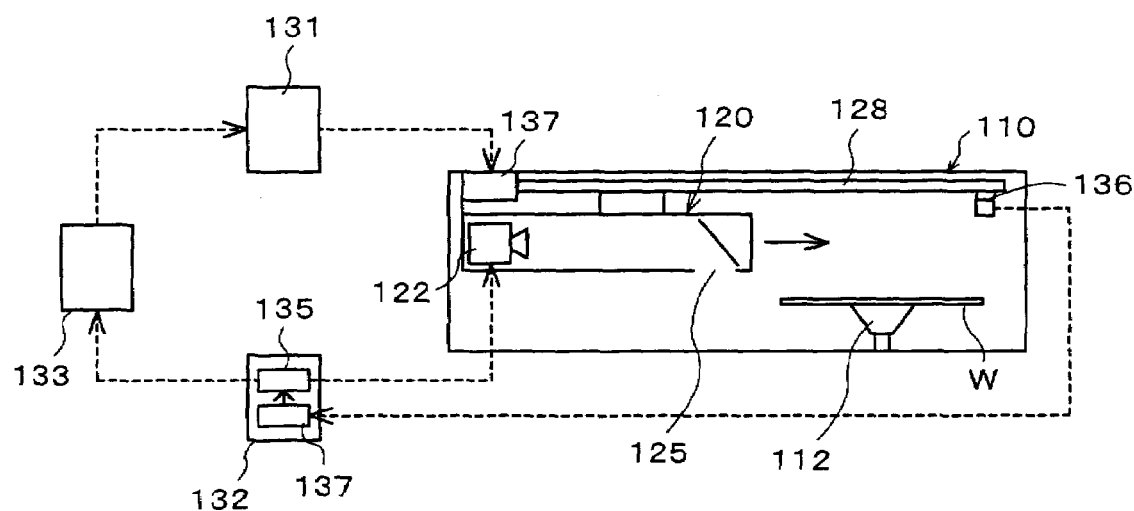
FIG. 9 is an explanatory view showing the outline of a configuration of a control system of a defect inspection apparatus according to another embodiment, including a light quantity adjusting unit.

The example shown in FIG. 9 shows a configuration to automatically control the length of the image capture cycle in such a case, in which a light quantity adjusting unit 137 in the second controller 132 is configured to output to the reference clock 135 a correction signal for correcting the image capture cycle based on a signal from a sensor 136, for example, provided in the defect inspection apparatus 110, for measuring the reflectivity of the front surface on top of the wafer W so that the brightness of the image captured by the image pickup device 122 falls within a predetermined brightness range which has been previously set. This configuration ensures that the length of the cycle of image capture by the image pickup device 122 is automatically corrected, according to which the driving signal to the drive unit 127 is also controlled. Accordingly, even when images of the wafers W different in reflectivity are picked up, image pickup by the image pickup device 122 and movement of the image pickup device 122 itself by the drive unit 127 can be synchronized to obtain precise images. Further, the defect inspection can be performed with the same reference even for a wafer W with a high reflectivity and a wafer W with a low reflectivity.

Incidentally, if the reflectivity of the front surface of the wafer being an inspection object has been previously known, it is not necessary to use the above-described sensor 136, and information about the wafer whose reflectivity has been known may be registered in the second controller 132, or a storage medium having such information recorded therein may be connected to the second controller 132 every inspection so that the information is read.

While the image pickup device 122 is moved to a position above the mounting table 112 to pick up an image of the wafer W on the mounting table 112 in the above case, the image pickup device 122 may be fixed and the mounting table 112 may be moved to pickup an image of the wafer W. Such a case will be described below.

Figure 10:
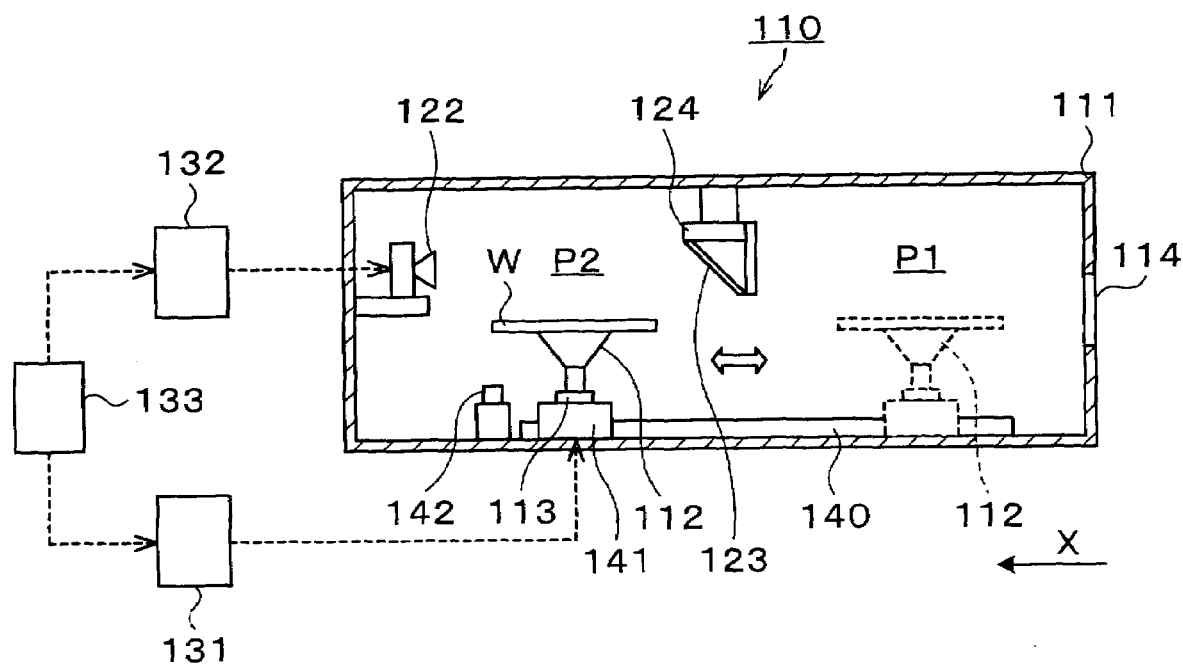
FIG. 10 is an explanatory view of a side section of a defect inspection apparatus according to another embodiment.

For example, as shown in FIG. 10, the image pickup device 122 is fixed to one end side (the left side in the X-direction in FIG. 10) in the casing 111 of the defect inspection apparatus 110. The half mirror 123 and the illumination device 124 are fixed near the middle in the X-direction of the casing 111. On the bottom surface of the casing 111, a guide rail 140 is provided which extends from the one end side to the other end side (the right side in the X-direction in FIG. 10). The mounting table 112 is provided on the guide rail 140 and can move in the X-direction along the guide rail 140 by means of a drive unit 141 such as a pulse motor. The transfer-in/out port 114 for the wafer W is provided in the side surface on the other end side of the casing 111.

The mounting table 112 is rotatable by the rotation drive unit 113 as in the above-described embodiment. On the one end side in the casing 111, a sensor 142 is provided which detects the position of a notch portion of the wafer W on the mounting table 112. Based on the detection result of the position of the notch portion by the sensor 142, the rotation drive unit 113 can rotate the mounting table 112 to align the angle of the wafer W.

The control system of the defect inspection apparatus 110 is the same as that in the above-described embodiment and includes a first controller 131 for controlling drive of the drive unit 141, a second controller 132 for controlling image pickup by the image pickup device 122, and a third controller 133 for controlling the first controller 131 and the second controller 132.

At the time when defect inspection of the wafer W, the wafer W is first transferred in through the transfer-in/out port 114 and mounted on the mounting table 112. At this time, the mounting table 112 is waiting in advance at a wafer transfer-in/out position P1 (a position shown by a dotted line in FIG. 10) on the other end side in the casing 111. Thereafter, the mounting table 112 is moved by the drive unit 141 to an alignment position P2 (a position shown by a solid line in FIG. 10) on the one end side in the casing 111 and stopped. Subsequently, the notch portion of the wafer W is detected by the sensor 142, and the wafer W is rotated based on the position of the notch portion, whereby the position of the notch portion of the wafer W is adjusted to a predetermined set angle (alignment of the wafer W). The set angle in this event is previously determined, for example, depending on the recipe of the wafer processing, and an angle is selected to allow acquisition of an optimum image. Thereafter, the mounting table 112 is moved by the drive unit 141 at a predetermined speed to the wafer transfer-in/out position P1 side, and the image pickup device 122 picks up an image of the front surface of the wafer W when the wafer W passes under the half mirror 123. The mounting table 112 is stopped at the wafer transfer-in/out position P1, and the wafer W is then transferred out of the transfer-in/out port 114.

Control of the drive unit 141 and the image pickup device 122 is conducted as in the above-described embodiment. For example, when driving the mounting table 112, the third controller 133 outputs the driving signal to the first controller 131, based on which the first controller 131 outputs a predetermined driving signal to the drive unit 141. In this event, the third controller 133 outputs the driving signal also to the second controller 132 at the same time, based on which the second controller 132 outputs the external synchronization signal to the image pickup device 122, based on which the image pickup device 122 picks up an image of the wafer W on the mounting table 112. Thus, the image pickup by the image pickup device 122 is synchronized with the movement of the mounting table 112.

As a result, even if the image pickup device 122 picks up an image of the wafer W on the mounting table 112 while the mounting table 112 is moving, a precise image can be obtained to realize a defect inspection with high precision. In addition, the optical system including the image pickup device 122, the half mirror 123, and the illumination device 124 is fixed, thus preventing displacement of the relative positions in the optical system, so that a precise image can be stably obtained. Further, the moving speed of the wafer W can be accordingly increased during the image pickup to improve the throughput of defect inspection.

Note that, in the embodiment in which the mounting table 112 is moved, a feedback signal, for example, an encoder signal, outputted from the drive unit 141 to the first controller 131 may be outputted directly to the second controller 132, or outputted to the second controller 132 via the third controller 133 as in the above-described embodiment, so that the second controller 132 may output the external synchronization signal to the image pickup device 122 based on the feedback signal. Furthermore, if the second controller 132 has a reference clock 135 being a reference for outputting the external synchronization signal to the image pickup device 122, image pickup by the image pickup device 122 may be synchronized with movement of the mounting table 112 by directly outputting the driving signal based on the reference clock 135 to the first controller 131 or outputting the driving signal to the first controller 131 via the third controller 133.

Figure 11:
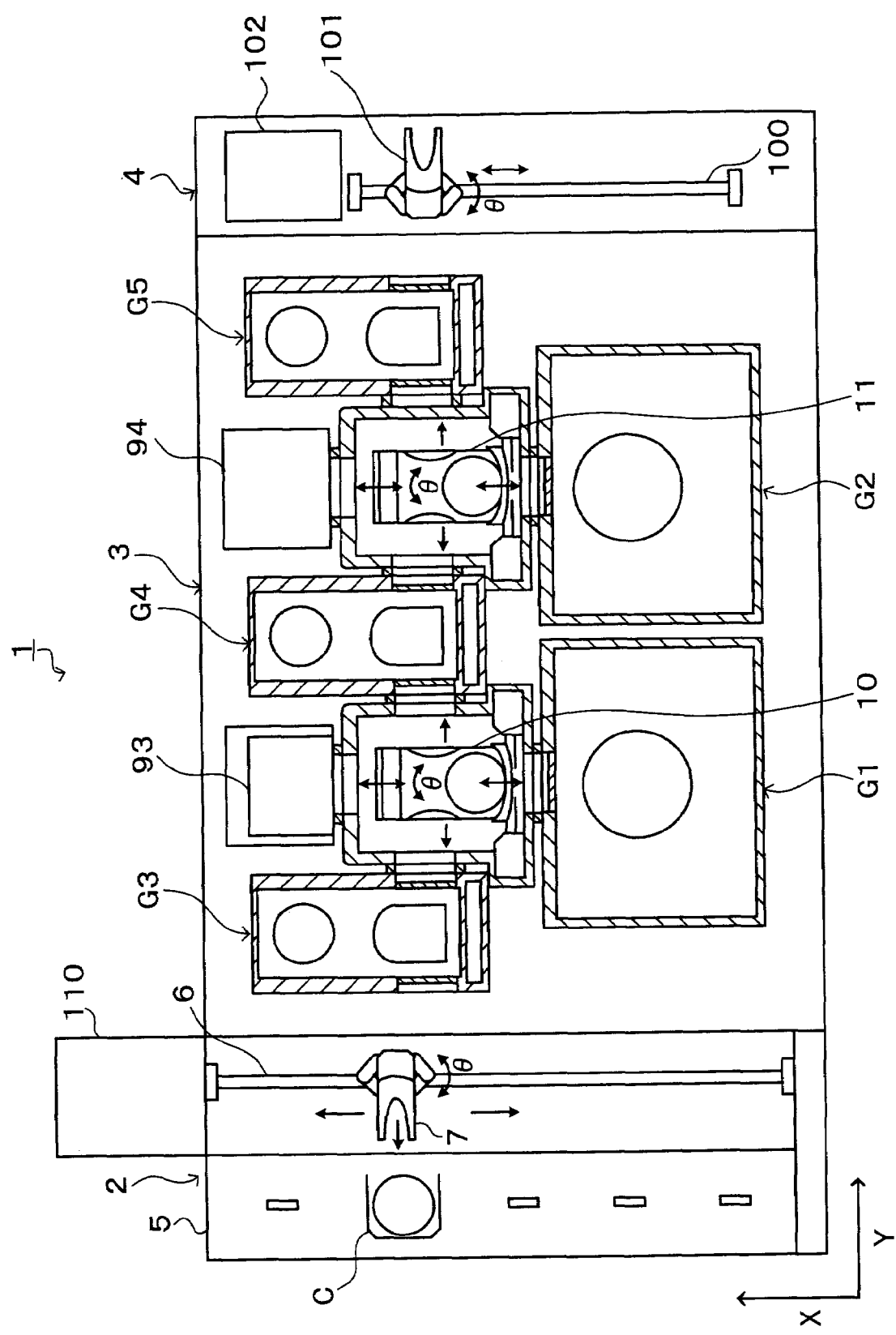
FIG. 11 is an explanatory view of the plane of a coating and developing treatment system including a defect inspection apparatus according to another embodiment.

In the above embodiment, the defect inspection apparatus 110 may be provided in the cassette station 2 as shown in FIG. 11. In this case, transfer of the wafer W to the defect inspection apparatus 110 may be performed by the wafer transfer body 7.

Figure 12:
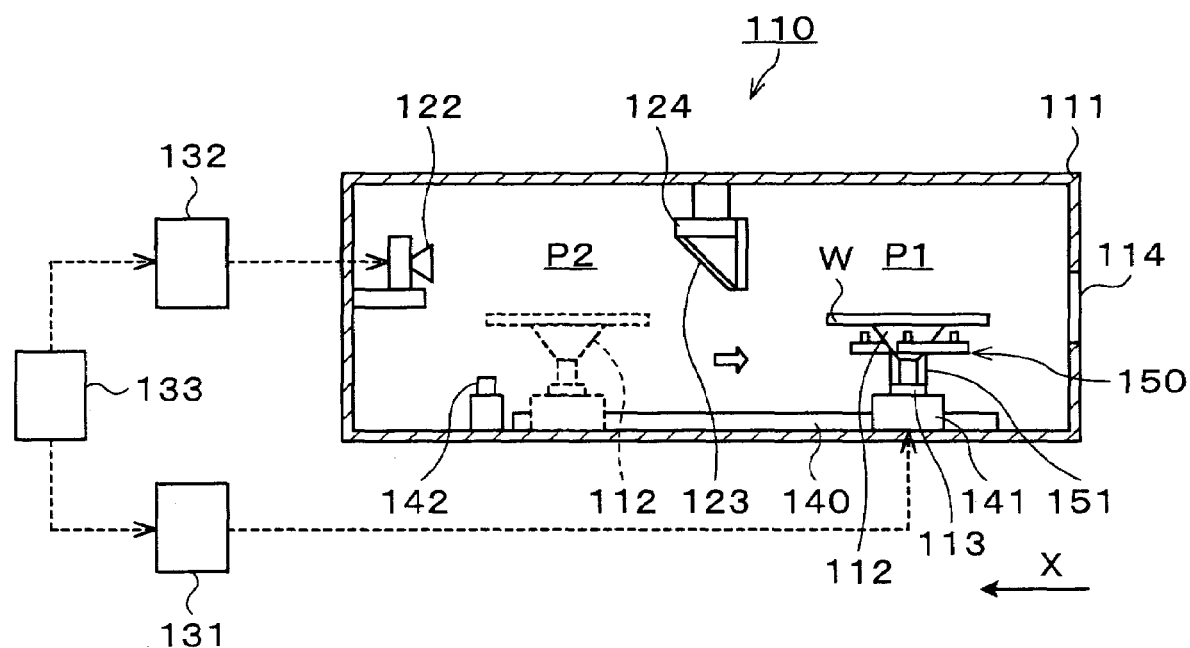
FIG. 12 is an explanatory view of a side section of a defect inspection apparatus according to another embodiment.
Figure 13:
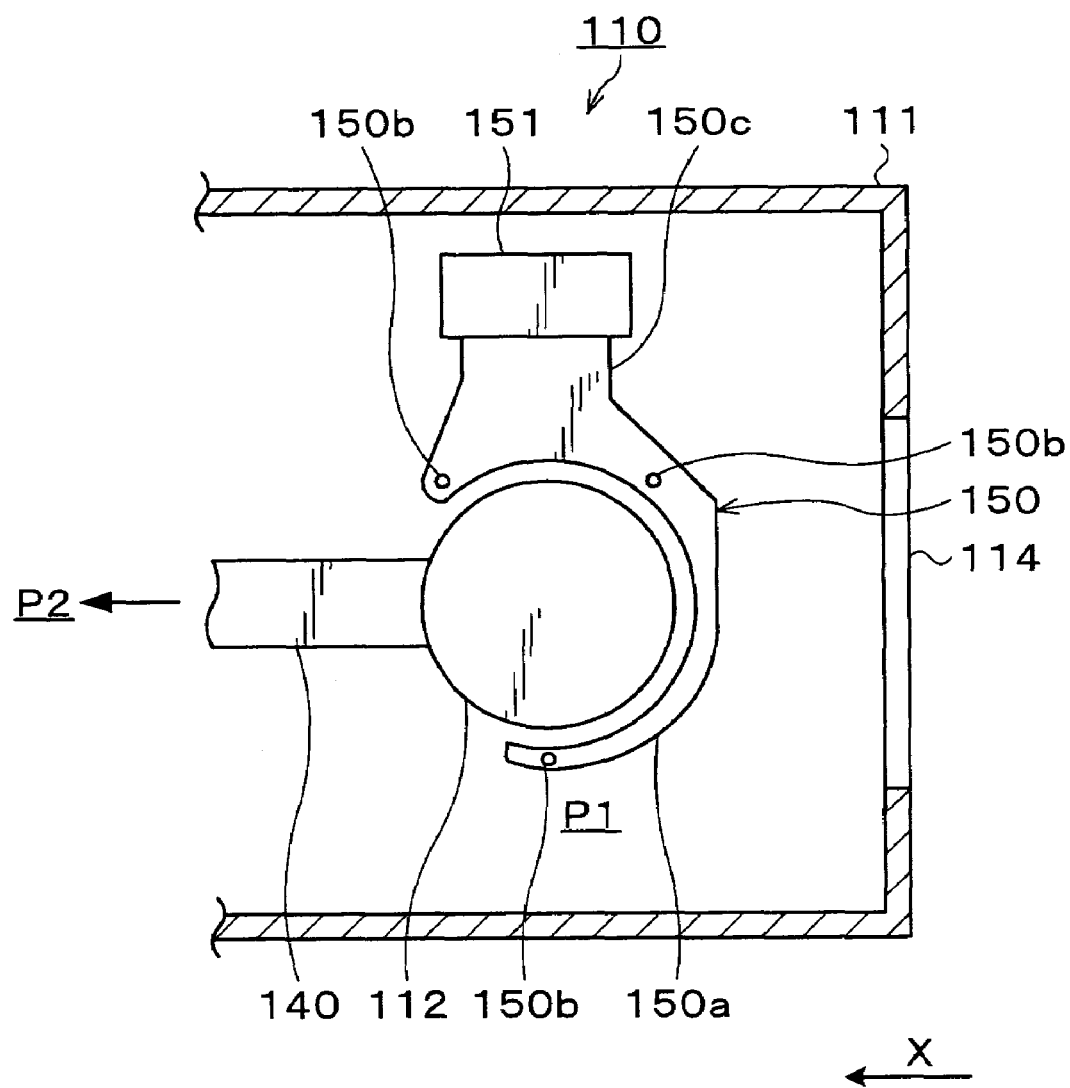
FIG. 13 is an explanatory view of a plane section of a portion of a defect inspection apparatus according to another embodiment.

Besides, if a single transfer arm accesses the defect inspection apparatus 110 like the wafer transfer body 7, the defect inspection apparatus 110 may include a buffer arm (a transfer member) for temporarily supporting the wafer W after image pickup. In this case, for example, a buffer arm 150 is provided at the wafer transfer-in/out position P1 in the casing 111 as shown in FIG. 12. The buffer arm 150 has, for example, a support portion 150*a* at its tip as shown in FIG. 13. The support portion 150*a* is formed, for example, in an almost C-shape. The diameter of the almost C-shape of the support portion 150*a* is greater than the diameter of the mounting table 112 so that the mounting table 112 can be enclosed within the support portion 150*a*. A cutout portion of the almost C-shape of the support portion 150*a* is formed on the alignment position P2 side in the casing 111, so that the mounting table 112 can be moved to the alignment position P2 side without interference with the support portion 150*a*. On the support portion 150*a*, a plurality of support pins 150*b* are provided to support the wafer W thereon. A base portion 150*c* of the buffer arm 150 is attached to a raising and lowering portion 151 such as a cylinder, thereby allowing the buffer arm 150 to be raised and lowered to above and below the mounting table 112.

Figure 14:
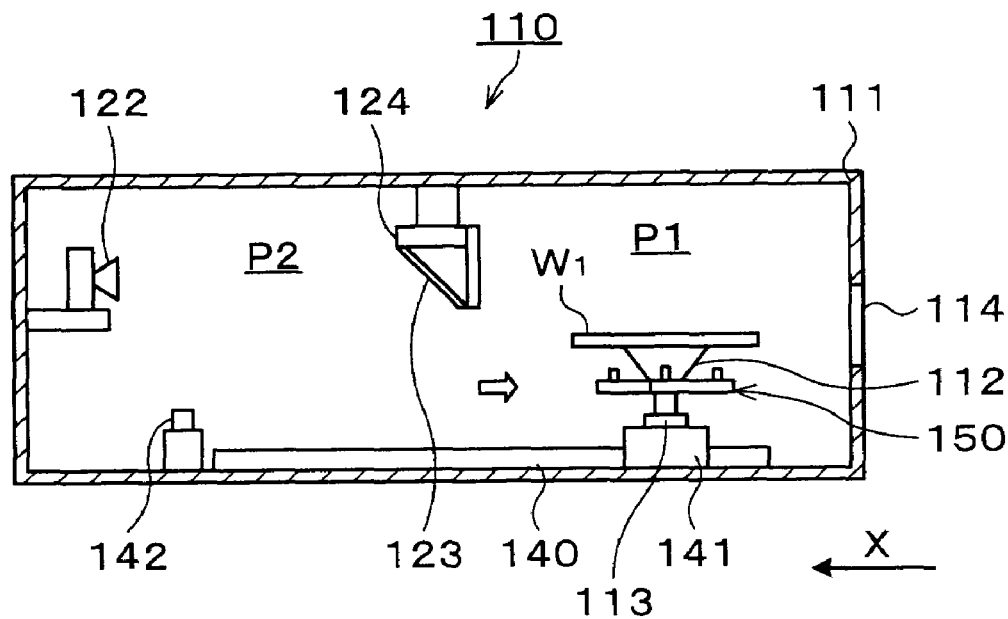
FIG. 14 is an explanatory view showing an appearance in the defect inspection apparatus when a wafer is returned by a mounting table to a wafer transfer-in/out position.
Figure 15:
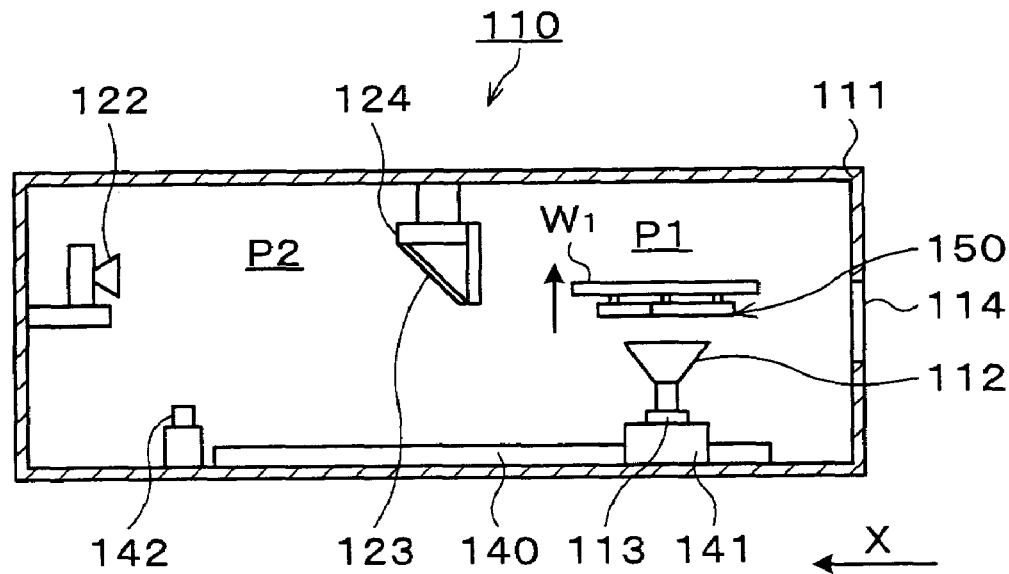
FIG. 15 is an explanatory view showing an appearance in the defect inspection apparatus when the wafer is lifted by a buffer arm.
Figure 16:
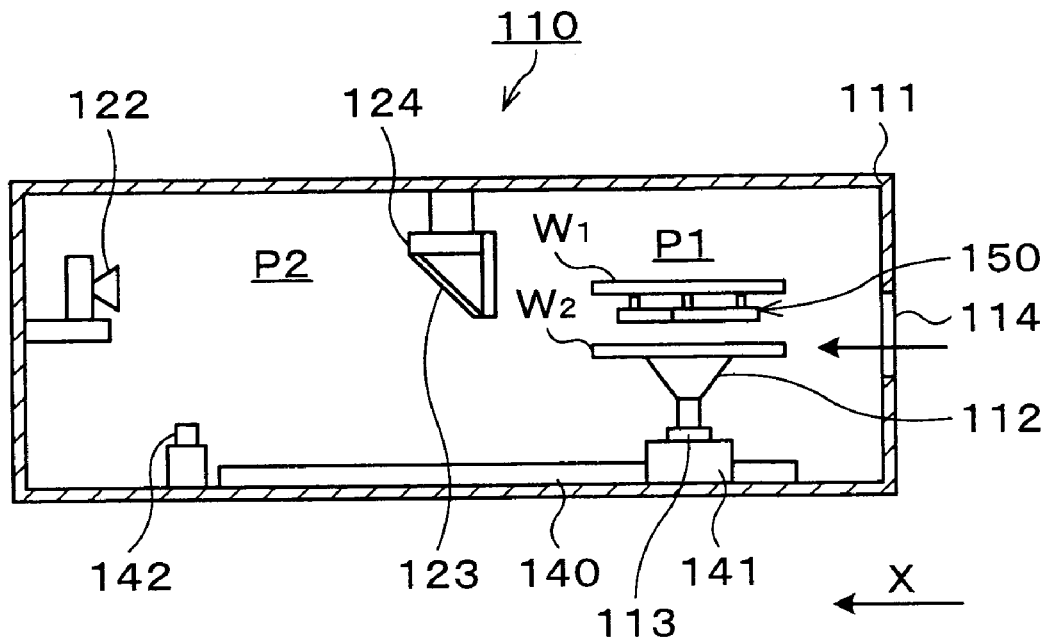
FIG. 16 is an explanatory view showing an appearance in the defect inspection apparatus when a next wafer is transferred thereinto.

At the time when transferring-in/out the wafer W to/from the defect inspection apparatus 110, after the pickup of the image of a wafer W1 is finished and the mounting table 112 is moved to the wafer transfer-in/out position P1 as shown in FIG. 14, the buffer arm 150 is raised to above the mounting table 112 so that the wafer W on the mounting table 112 is supported and lifted by the buffer arm 150 as shown in FIG. 15. In this state, a next wafer W2 is transferred in through the transfer-in/out port 114 by the wafer transfer body 7 and mounted on the mounting table 112 as shown in FIG. 16.

Figure 17:
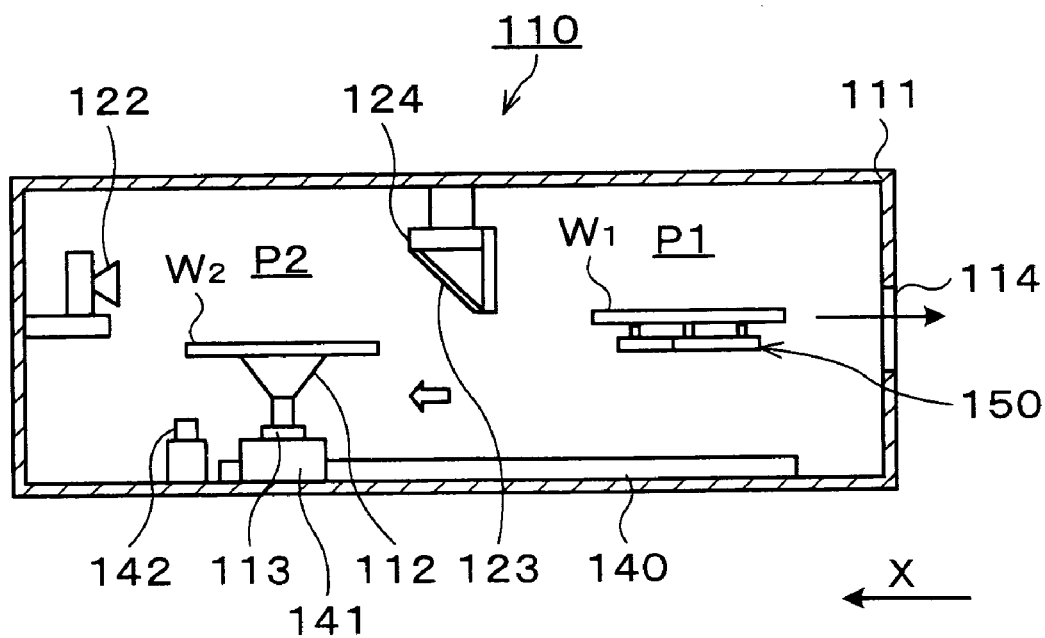
FIG. 17 is an explanatory view showing an appearance in the defect inspection apparatus when the preceding wafer is transferred therefrom.
Figure 18:
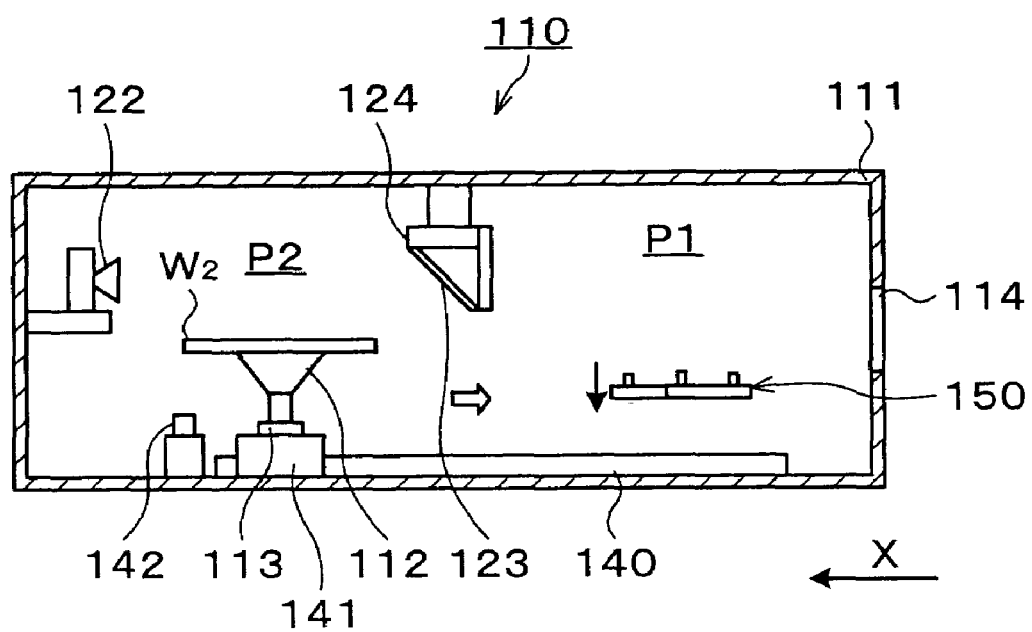
FIG. 18 is an explanatory view showing an appearance in the defect inspection apparatus when the buffer arm is lowered.

The wafer W1 is then delivered from the buffer arm 150 to the wafer transfer body 7 and transferred out through the transfer-in/out port 114 by the wafer transfer body 7 as shown in FIG. 17. Besides, the wafer W2 is moved to the alignment position P2 by the mounting table 112. While the mounting table 112 is moving to the alignment position P2 side, the buffer arm 150 is lowered to a position lower than the mounting table 112 as shown in FIG. 18. Thereafter, the mounting table 112 is returned to the wafer transfer-in/out position P1, while image pickup of the wafer W2 is being performed. Thereafter, the buffer arm 150 is raised again to lift the wafer W2 to above the mounting table 112. In this state, a next wafer is mounted on the mounting table 112 by the wafer transfer body 7. These actions are repeated to perform defect inspection for a plurality of wafers in succession.

According to this example, even a single transfer arm can smoothly deliver the wafers W to the defect inspection apparatus 110, thereby improving the processing efficiency of inspection by the defect inspection apparatus 110.

Although the first controller 131, the second controller 132, and the third controller 133 are configured as discrete units in each of the above-described embodiments, it is only required to essentially provide a controller substantially having a function of conducting the controls performed by the above controllers, and therefore it is not always necessary to embody the controllers as discrete units.

Note that although the inspection object, that is, the substrate to be image-picked up by the image pickup device 122 is a semiconductor wafer in the above-described embodiments, the present invention is applicable, not limited to the above, but even to substrates, for example, for various kinds of flat displays as a matter of course.

The present invention is useful in performing a surface inspection using an image of a substrate.

What is claimed is:

1. A defect inspection method of picking up an image of a substrate on a mounting table by an image pickup device while relatively moving the image pickup device and the substrate in a predetermined direction to inspect the substrate for a defect,
    wherein drive of the image pickup device or the mounting table to realize the relative movement is synchronized with the image pickup by the image pickup device when the image pickup device picks up the image of the substrate.

2. The defect inspection method as set forth in claim 1,
    wherein image capture by the image pickup device is controlled based on a driving signal outputted from a controller to a drive unit for driving the image pickup device or the mounting table.

3. The defect inspection method as set forth in claim 1,
    wherein image capture by the image pickup device is controlled based on a feedback signal outputted to a controller from a drive unit for driving the image pickup device or the mounting table.

4. The defect inspection method as set forth in claim 1,
    wherein drive of the image pickup device or the mounting table is controlled based on a control signal for controlling a timing of image capture by the image pickup device.

5. The defect inspection method as set forth in claim 4,
    wherein the image capture timing is changed depending on a luminance on the substrate.

6. The defect inspection method as set forth in claim 1,
    wherein the image pickup device picks up the image of the substrate on the mounting table with the image pickup device fixed and the mounting table being moved with respect to the image pickup device.

7. A defect inspection apparatus for picking up an image of a substrate on a mounting table by an image pickup device while relatively moving said image pickup device and the substrate on said mounting table in a predetermined direction by a drive unit to inspect the substrate for a defect, comprising:
    a first controller for controlling said drive unit; and
    a second controller for controlling the image pickup by said image pickup device,
    wherein a driving signal outputted from said first controller or outputted to said first controller in order to drive said drive unit is outputted also to said second controller, and said second controller controls the image pickup by said image pickup device based on the driving signal.

8. A defect inspection apparatus for picking up an image of a substrate on a mounting table by an image pickup device while relatively moving said image pickup device and the substrate on said mounting table in a predetermined direction by a drive unit to inspect the substrate for a defect, comprising:
    a first controller for controlling said drive unit; and
    a second controller for controlling the image pickup by said image pickup device,
    wherein a feedback signal outputted from said drive unit to said first controller is outputted also to said second controller from said first controller directly or via another controller, and said second controller controls the image pickup by said image pickup device based on the feedback signal.

9. A defect inspection apparatus for picking up an image of a substrate on a mounting table by an image pickup device while relatively moving said image pickup device and the substrate on said mounting table in a predetermined direction by a drive unit to inspect the substrate for a defect, comprising:
    a first controller for controlling said drive unit; and
    a second controller for controlling the image pickup by said image pickup device,
    wherein said second controller includes a reference clock for controlling a timing of image capture by said image pickup device, a driving signal is outputted to said first controller directly or via another controller based on said reference clock, and said first controller controls said drive unit based on the driving signal.

10. The defect inspection apparatus as set forth in claim 9, further comprising:
    a control unit for changing a cycle of said reference clock based on luminance information on the substrate being an image pickup object.

11. The defect inspection apparatus as set forth in claim 9,
    wherein said reference clock is provided in said image pickup device or the other controller.

12. The defect inspection apparatus as set forth in claim 7,
    wherein said image pickup device picks up the image of the substrate on said mounting table with said image pickup device fixed and said mounting table being moved with respect to said image pickup device by said drive unit.

13. The defect inspection apparatus as set forth in claim 8, wherein said image pickup device picks up the image of the substrate on said mounting table with said image pickup device fixed and said mounting table being moved with respect to said image pickup device by said drive unit.

14. The defect inspection apparatus as set forth in claim 9, wherein said image pickup device picks up the image of the substrate on said mounting table with said image pickup device fixed and said mounting table being moved with respect to said image pickup device by said drive unit.

15. A computer readable storage medium storing a program running on a computer in a control unit for controlling a defect inspection apparatus for causing the defect inspection apparatus to perform a substrate defect inspection method, said defect inspection method comprising:

picking up an image of a substrate on a mounting table by an image pickup device while relatively moving the image pickup device and the substrate in a predetermined direction to inspect the substrate for a defect, wherein drive of the image pickup device or the mounting table to realize the relative movement is synchronized with the image pickup by the image pickup device when the image pickup device picks up the image of the substrate.

* * * * *